US010973481B2

(12) United States Patent
Yoshida

(10) Patent No.: US 10,973,481 B2
(45) Date of Patent: Apr. 13, 2021

(54) RADIOGRAPHIC SYSTEM

(71) Applicant: Shimadzu Corporation, Kyoto (JP)

(72) Inventor: Takanori Yoshida, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 16/366,770

(22) Filed: Mar. 27, 2019

(65) Prior Publication Data

US 2019/0320991 A1    Oct. 24, 2019

(30) Foreign Application Priority Data

Apr. 23, 2018    (JP) .............................. JP2018-082085

(51) Int. Cl.
*H05G 1/64* (2006.01)
*A61B 6/00* (2006.01)

(52) U.S. Cl.
CPC .............. *A61B 6/504* (2013.01); *A61B 6/462* (2013.01); *A61B 6/481* (2013.01); *A61B 6/4494* (2013.01);
(Continued)

(58) Field of Classification Search
CPC ......... A61B 6/12; A61B 6/4494; A61B 6/462; A61B 6/463; A61B 6/464; A61B 6/481; A61B 6/487; A61B 6/504; A61B 6/5235; A61B 6/542; A61B 6/548; A61B 5/0044; A61B 5/055; A61B 6/032; A61B 6/469; A61B 6/503; A61B 6/5264; A61B 6/5288; A61B 1/00; A61B 2034/2057; A61B 2034/2065; A61B 2090/371; A61B 34/10; A61B 34/20; A61B 6/482; A61B 90/39; A61B 6/06; A61B 6/4028; A61B 6/4042; A61B 2090/3966; A61B 6/541; A61B 5/0035; A61B 5/0066; A61B 5/0084; A61B 6/4441; A61B 6/486; A61B 6/547; A61B 6/4405; A61B 6/507; A61B 6/5241; A61B 2017/00128; A61B 2018/00577; A61B 2018/00589; A61B 2018/00642;
(Continued)

(56) References Cited

U.S. PATENT DOCUMENTS 7,941,000 B2    5/2011    Rongen et al.
2005/0020911 A1*  1/2005  Viswanathan ......... A61B 6/463
600/424
(Continued)

FOREIGN PATENT DOCUMENTS

JP    5739811 B2    6/2015
JP    5867306 B2    2/2016
JP    5886390 B2    3/2016

*Primary Examiner* — Irakli Kiknadze
(74) *Attorney, Agent, or Firm* — Muir Patent Law, PLLC

(57) ABSTRACT

A controller generates, based on a position of a marker in an X-ray image, an intermediate image in which a device inserted into a subject's body is displayed. After the generation of the intermediate image, the controller matches the marker of the X-ray image with a marker of the intermediate image based on the position of the marker in the X-ray image and a position of a marker in the intermediate image to align the X-ray image and the intermediate image with each other every time the X-ray image is newly generated. The controller then controls the display to display an overlaid image generated by overlaying the X-ray image and the intermediate image aligned with each other.

18 Claims, 10 Drawing Sheets

(52) U.S. Cl.
CPC ............... *A61B 6/464* (2013.01); *A61B 6/542* (2013.01); *A61B 6/548* (2013.01)

(58) Field of Classification Search
CPC .. A61B 2018/0066; A61B 2018/00797; A61B 2018/00803; A61B 6/027; A61B 6/466; G06T 11/60; G06T 2207/10081; G06T 15/08; G06T 19/003; G06T 2200/04; G06T 2207/10012; G06T 2207/10121; G06T 2207/30016; G06T 2207/30061; G06T 2207/30196; G06T 2207/30204; G06T 2210/41; G06T 2211/428; G06T 2219/008; G06T 2219/2016; G06T 7/0012; G06T 7/33; G06T 2207/20221; G06T 2207/30101; G06T 3/0068; G06T 2207/30036; G06T 17/00; G06T 19/006; G06T 2215/16; G06T 11/008; G06T 19/20; G06T 2219/2004; G06T 2207/10104; G06T 7/11; G06T 2207/10116; G06T 2207/30048; G06T 11/005; G06T 2207/10076; G06T 2211/424; G06T 7/174; G06T 7/38; G06T 11/006; G06T 2200/08; G06T 2207/10132; G06T 2207/20016; G06T 7/13; G06T 2207/10072; G06T 2207/10124; G06T 2207/20212; G06T 2207/30004; G06T 2207/30096; G06T 2207/30104; G06T 3/20; G06T 3/4053; G06T 7/215; H01J 35/14; H05G 1/10; H05G 1/64; G06K 2209/057; G06K 9/3241; G06K 9/6256; G06K 2209/05; G06K 9/38; G01N 2223/419; G01N 23/046; G01N 2223/076; G01N 23/223; G01N 23/2204; G01N 2500/04; G01N 33/566; A61C 5/44; A61C 19/04; A61C 19/041; A61C 19/042; A61C 1/082; A61C 5/40; A61C 5/42; A61C 7/002; A61C 9/004; A61N 7/02; A61M 2210/12; A61M 5/007; G16H 50/30; H04N 7/18; B64C 2201/127; F21V 11/12; F21V 1/08; F21V 1/10; F21V 7/005; G02B 27/017
USPC ......................... 378/4, 19, 98.2, 62
See application file for complete search history.

(56) References Cited

U.S. PATENT DOCUMENTS

| | | | |
|---|---|---|---|
| 2007/0297658 A1* | 12/2007 | Camus | G06T 7/0012 382/130 |
| 2008/0031405 A1* | 2/2008 | Matsumoto | A61B 6/466 378/8 |
| 2009/0074267 A1* | 3/2009 | Pedrizzetti | A61B 8/06 382/128 |
| 2010/0104167 A1 | 4/2010 | Sakaguchi et al. | |
| 2010/0185087 A1* | 7/2010 | Nields | A61B 6/0492 600/439 |
| 2011/0216092 A1 | 9/2011 | Florent et al. | |
| 2014/0051991 A1 | 2/2014 | Sakaguchi et al. | |
| 2014/0204124 A1* | 7/2014 | Auvray | A61B 6/5235 345/634 |
| 2017/0065235 A1 | 3/2017 | Sakaguchi et al. | |
| 2017/0165008 A1* | 6/2017 | Finley | A61B 6/547 |
| 2018/0317865 A1 | 11/2018 | Sakaguchi et al. | |

* cited by examiner

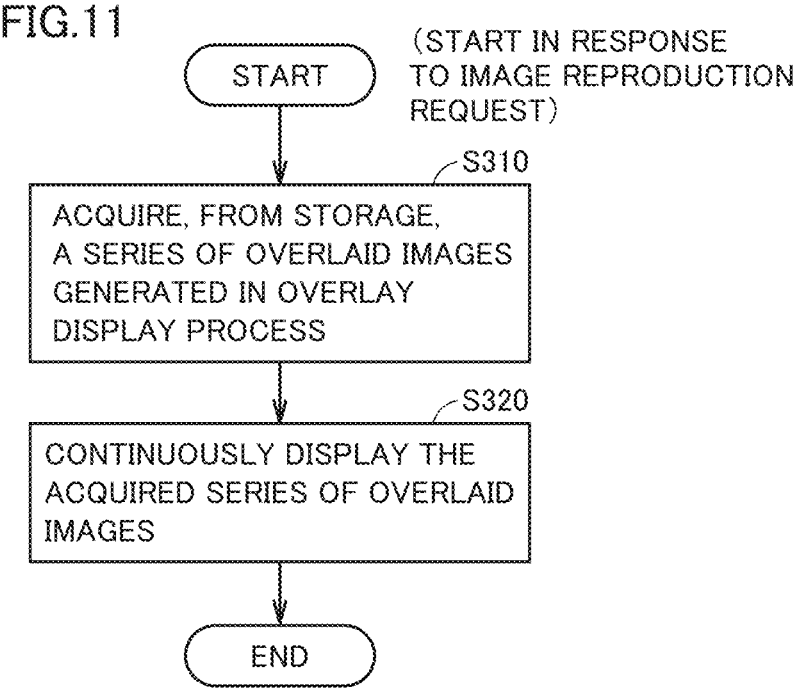

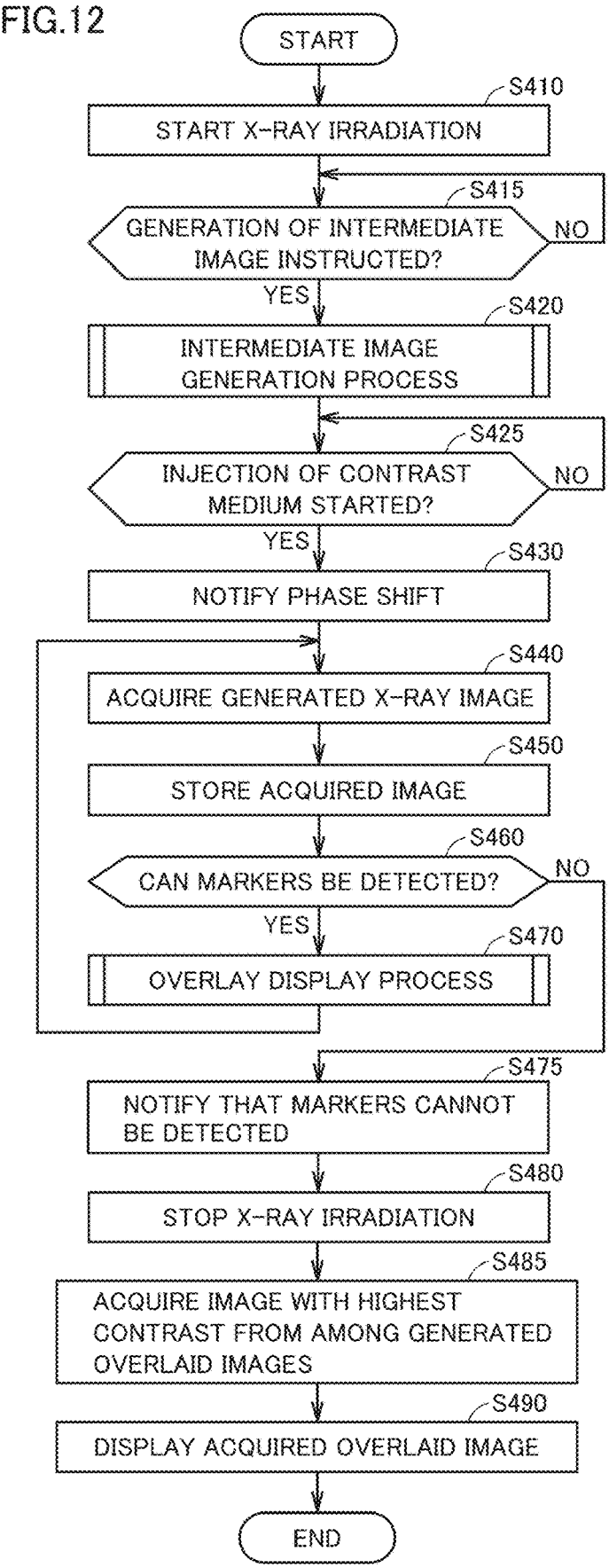

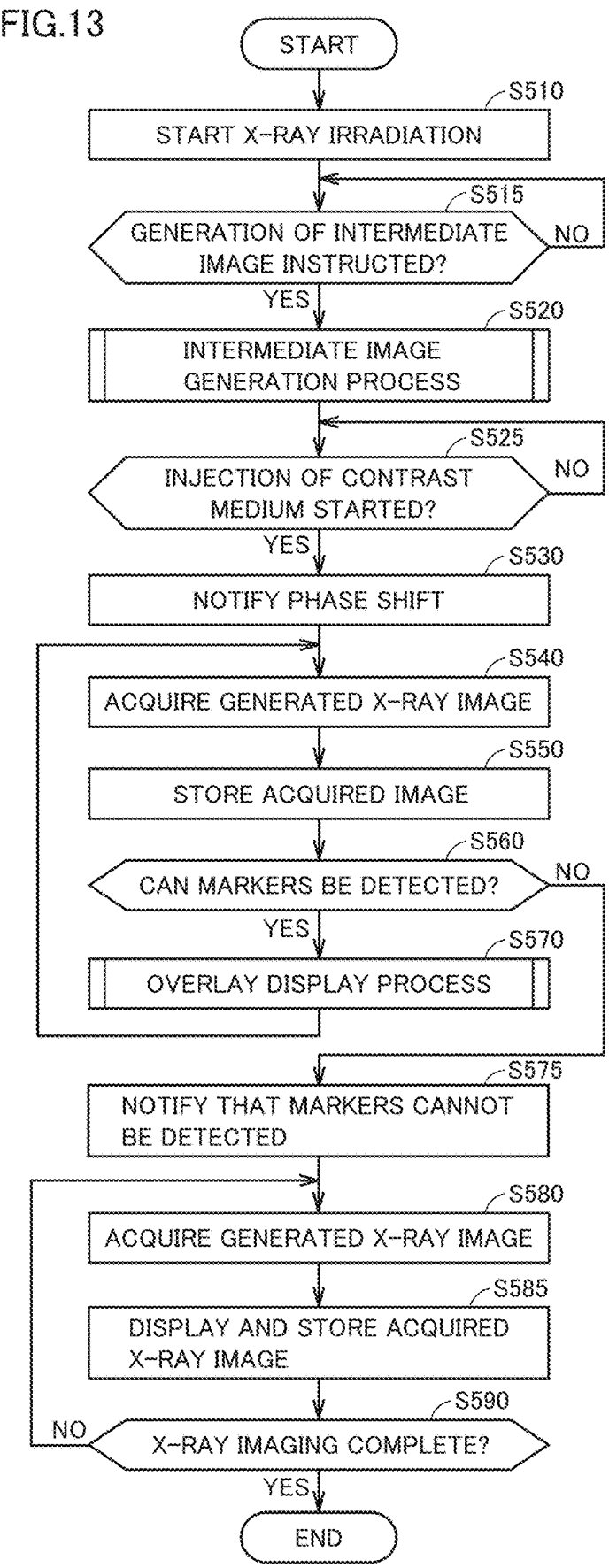

RADIOGRAPHIC SYSTEM

This nonprovisional application is based on Japanese Patent Application No. 2018-082085 filed on Apr. 23, 2018 with the Japan Patent Office, the entire contents of which are hereby incorporated by reference.

BACKGROUND OF THE INVENTION

Field of the Invention

The present invention relates to radiographic systems.

Description of the Background Art

In intervention treatments in which a catheter is inserted into a blood vessel and a device such as a stent is retained at an affected area in the blood vessel, it is desirable that the positional relationship and the degree of adhesion between the device and the blood vessel be checked on a display.

U.S. Pat. No. 7,941,000 discloses a technique of displaying an X-ray image, in which a device inserted into a blood vessel is displayed, and an X-ray image, in which a blood vessel (blood flow) visualized by injection of a contrast medium into the blood vessel is displayed while overlaying these X-ray images. In the technique described in U.S. Pat. No. 7,941,000, a series of recorded images (a plurality of raw images) from start to end of imaging are divided into a frame group (first subset) recorded without injection of the contrast medium and the other frame group (second subset) recorded with injection of the contrast medium. Then, an intermediate image is generated from the first subset, a mask image is selected from the second subset, and subsequently, the generated intermediate image and the selected mask image are displayed while being overlaid on each other.

In the technique described in U.S. Pat. No. 7,941,000, a series of images taken from start to end of imaging are recorded (stored), and an intermediate image (static image) generated from the recorded first subset and a mask image (static image) selected from the recorded second subset are displayed while being overlaid on each other. The technique described in U.S. Pat. No. 7,941,000 generates a display image based on the recorded (stored) images taken in the past, and thus, has a problem with real-time display.

SUMMARY OF THE INVENTION

The present invention has been made to solve the above problem, and has an object to provide a radiographic system that can display a taken X-ray image together with an image, in which a device is displayed, in real time.

A first aspect of the present invention relates to a radiographic system. The radiographic system includes an imaging apparatus configured to irradiate the subject with X-rays and sequentially generate an X-ray image of the subject, a display configured to display the X-ray image generated by the imaging apparatus, and a controller configured to control the display. The controller is configured to generate, based on a position of a marker in the X-ray image, an intermediate image in which a device is displayed from the X-ray image, where the device is inserted into a body of the subject. The controller is configured to, after the generation of the intermediate image, match the marker in the X-ray image with a marker in the intermediate image based on the position of the marker in the X-ray image and a position of the marker in the intermediate image to align the X-ray image and the intermediate image with each other every time the X-ray image is newly generated. The controller is configured to control the display to display an overlaid image generated by overlaying the X-ray image and the intermediate image aligned with each other.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIG. 11 is a flowchart showing an example procedure of an image reproduction process.

FIG. 12 is a flowchart showing an example procedure of processes performed by a control device in Variation 1.

FIG. 13 is a flowchart showing an example procedure of processes performed by a control device in Variation 2.

DESCRIPTION OF THE PREFERRED EMBODIMENTS

Figure 1:
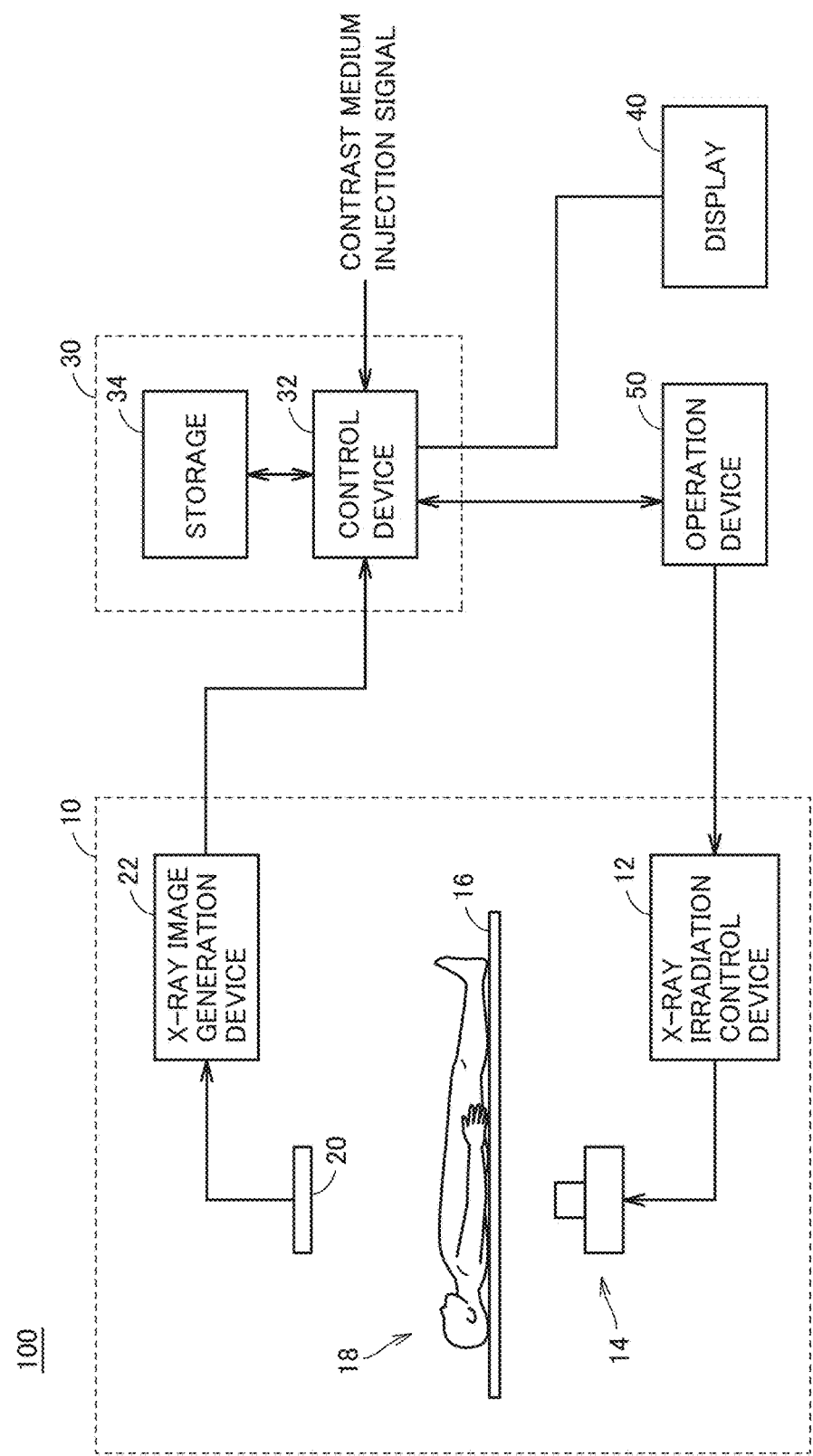
FIG. 1 shows an overall configuration of a radiographic system according to embodiments of the present invention.

Embodiments of the present invention will now be described in detail referring to the drawings. It should be noted that in the following drawings, the same or corresponding parts are denoted by the same reference numerals, and the description thereof will not be repeated.

[Overall Configuration of Radiographic System]

FIG. 1 shows an overall configuration of a radiographic system according to embodiments of the present invention. Referring to FIG. 1, a radiographic system 100 includes an imaging apparatus 10, a controller 30, a display 40, and an operation device 50.

Imaging apparatus 10 includes an X-ray irradiation control device 12, an X-ray irradiation device 14, an imaging table 16, an X-ray image detection device 20, and an X-ray image generation device 22. X-ray irradiation control device 12 controls start/end of X-ray irradiation and controls imaging conditions such as tube voltage and tube current in accordance with an instruction from operation device 50.

X-ray irradiation device 14 includes an X-ray tube, a collimator, and a moving device (which are not shown).

X-ray irradiation device 14 generates X-rays in accordance with the imaging conditions set by X-ray irradiation control device 12 and applies the X-rays toward a subject 18 on imaging table 16. The X-ray tube is attached to the moving device and is movable vertically and horizontally by the moving device. The collimator is provided in the X-ray tube and adjusts an irradiation field of X-rays applied from the X-ray tube.

X-ray image detection device 20 detects X-rays which have been applied from the X-ray tube and passed through imaging table 16 and subject 18. X-ray image detection device 20 is representatively formed of a flat panel detector (hereinafter referred to as "FPD"). The FPD may be an indirect FPD that converts incident X-rays into fluorescence by a phosphor and then convert the fluorescence into an electric signal or a direct FPD that directly converts incident X-rays into an electric signal by an X-ray conversion film such as amorphous selenium (a-Se).

X-ray image generation device 22 acquires an electric signal converted from the incident X-rays in X-ray image detection device 20 from X-ray image detection device 20 per predetermined period, generates an X-ray image, and then outputs the X-ray image to controller 30. X-ray image generation device 22 sequentially generates X-ray images of 15 frames per second and outputs the X-ray images to controller 30.

Controller 30 includes a control device 32 and a storage 34. Control device 32 includes a processing unit, memories (read only memory (ROM) and random access memory (RAM)), and an input-output buffer for inputting and outputting various signals (which are not shown). Control device 32 acquires the X-ray images sequentially generated by X-ray image generation device 22 from X-ray image generation device 22 and performs various processes on the acquired X-ray images in accordance with a program stored in the memory (ROM). Control device 32 subsequently controls display 40 to display an X-ray image subjected to the various processes. Specific details of the processes performed by control device 32 will be described below in detail.

Storage 34 includes, for example, a mass storage unit such as hard disk or solid state drive. Storage 34 stores data of the X-ray image taken by imaging apparatus 10. Storage 34 also stores data of an image displayed on display 40 during reproduction after the completion of imaging by imaging apparatus 10.

Display 40 displays an X-ray image generated by imaging apparatus 10. Display 40 receives, from controller 30, data of the X-ray image subjected to various processes in controller 30 and displays the X-ray image. Display 40 is formed of, for example, a display including a touch panel. An image displayed on display 40 will also be described below together with the process of control device 32.

Operation device 50 is an input device that can be operated by a doctor or technician who uses radiographic system 100 (hereinafter referred to as a "user" of radiographic system 100). The user of radiographic system 100 can, for example, instruct start/end of X-ray imaging by imaging apparatus 10, set imaging conditions of imaging apparatus 10, and instruct a display state of display 40, through operation device 50.

Figure 2:
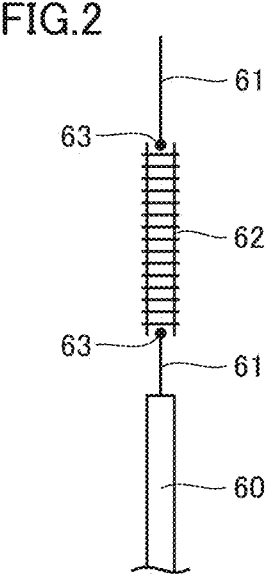
FIG. 2 schematically shows a configuration of a catheter for use in intervention treatments using the radiographic system.

FIG. 2 schematically shows a configuration of a catheter for use in intervention treatments using radiographic system 100. Referring to FIG. 2, a catheter 60 includes a guide wire 61 therein. Guide wire 61 is provided with a device 62. Device 62 is, for example, a stent that is made of metal such as stainless steel and has a tubular mesh shape. With catheter 60, device 62 is disposed at a strictured area in a blood vessel, and device 62 is inflated by a balloon (not shown) provided in device 62 and is retained at the strictured area. Consequently, the strictured area can be widened to maintain a blood flow in normal state.

Markers 63 for identifying a position of device 62 during X-ray imaging are provided near device 62. In this example, a pair of markers 63 are provided at opposite ends of device 62 in guide wire 61. Marker 63 is, for example, a member that is made of metal such as gold, platinum, or tantalum and does not allow X-rays to pass therethrough. The position of device 62 can be identified by detecting the positions of markers 63 in a taken X-ray image.

[Display of Taken X-ray Image]

In intervention treatments in which a catheter is used to retain a device in a blood vessel, the device (stent) is inserted into the blood vessel after continuous X-ray imaging of a subject by an X-ray imaging apparatus, and when the insertion of the device is checked, a contrast medium is injected to visualize the blood vessel, thereby checking the positional relationship between the device and the blood vessel (affected area).

At this time, in one technique as described in U.S. Pat. No. 7,941,000, a series of taken images that record from start to end of imaging are divided into a frame group before the injection of the contrast medium and a frame group after the injection of the contrast medium, and an intermediate image (an image in which the device is displayed) generated from the frame group before the injection of the contrast medium and a blood vessel image (an image in which a blood vessel visualized by the contrast medium is displayed) appropriately selected from the frame group after the injection of the contrast medium are displayed while being overlaid on each other.

This technique, however, generates a display image based on a series of recorded (stored) images taken in the past and fails to perform an intervention treatment while checking the subject's state in real time.

Considering the above, radiographic system 100 according to the present embodiment provides a system that can display a taken X-ray image on display 40 in real time. Radiographic system 100 divides an imaging section from start to end of imaging of subject 18 into an intermediate image generation phase and a blood vessel display phase between before and after the injection of the contrast medium.

Figure 3:
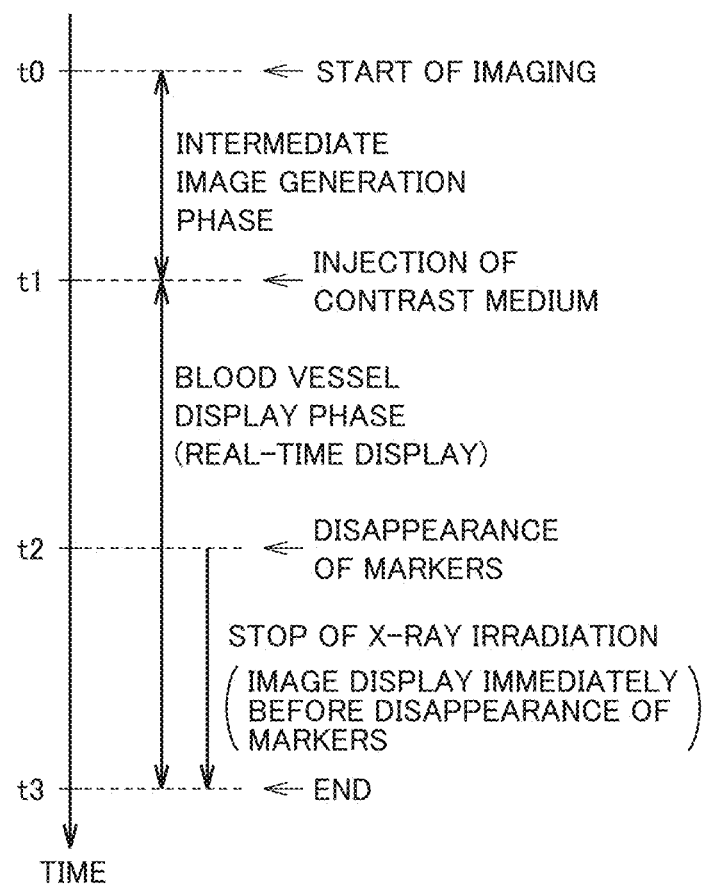
FIG. 3 shows an outline of a process flow in the radiographic system.

FIG. 3 shows an outline of a process flow in radiographic system 100. Referring to FIG. 3, imaging apparatus 10 starts imaging subject 18 at a time t0.

A phase from time t0 to a time t1 at which the injection of a contrast medium is started is an intermediate image generation phase. In the intermediate image generation phase, an intermediate image in which device 62 before the injection of the contrast medium is displayed is generated. In the present embodiment, a plurality of X-ray images before the injection of the contrast medium are aligned with each other based on the positions of markers 63 (FIG. 2) and then overlaid on each other, thereby generating an intermediate image. For the alignment of images, based on the positions of the pair of markers 63, the images are aligned with each other by moving, scaling up or down, or rotating the images to be overlaid on each other.

X-ray images used to generate an intermediate image may not necessarily be all the images taken from time t0 at which imaging is started to time t1 at which the injection of the contrast medium is started. For example, an intermediate image may be obtained by overlaying eight to a dozen or so X-ray images on one another, which are taken after a user's instruction to generate an intermediate image.

When an intermediate image is generated in the intermediate image generation phase and the injection of the contrast medium is started at time t1, the intermediate image generation phase shifts to the blood vessel display phase. In the blood vessel display phase, an X-ray image in which a blood vessel (blood flow) visualized by the injection of the contrast medium is displayed is generated. Then, every time an X-ray image is newly generated, an overlaid image obtained by overlaying the intermediate image generated in the intermediate image generation phase on the newly generated X-ray image is generated, and the overlaid image is displayed on display 40.

For alignment of a newly generated X-ray image and an intermediate image, based on the positions of markers 63 which are detected in the generated X-ray image and the positions of markers 63 in the intermediate image, the generated X-ray image and the intermediate image are aligned with each other by matching markers 63 of the intermediate image with markers 63 of the generated X-ray image. That is to say, as in the generation of the intermediate image, based on the positions of the pair of markers 63, images are moved, scaled up or down, or rotated to cause a pair of markers 63 of the generated X-ray image and a pair of markers 63 of the intermediate image to be overlaid on each other so that both the images are aligned with each other.

That is to say, in this blood vessel display phase, a desired image (e.g., an image in which markers 63 can be detected clearly) is not selected and overlaid on an intermediate image after collection of a series of taken X-ray images in which a blood vessel visualized by the contrast medium is displayed, but an image on which an intermediate image is overlaid is displayed on display 40 in real time every time an X-ray image is newly generated. Consequently, an intervention treatment can be performed while checking the subject's state in real time.

The injection of the contrast medium reduces the visibility of markers 63. Then, when markers 63 disappear (markers 63 can no longer be detected) in an X-ray image as the injection of the contrast medium progresses at a time t2, in the present embodiment, X-ray irradiation is stopped, and an image displayed immediately before the disappearance of markers 63 is held in display 40 (hereinafter, the holding of an image is also referred to as "last image hold").

That is to say, in the present embodiment, alignment with an intermediate image cannot be performed if markers 63 can no longer be detected due to the contrast medium, and thus, an overlaid image (last image) of an intermediate image and a latest X-ray image, in which markers 63 have been detected, in place of a newly generated X-ray image, is displayed on display 40 (last image hold). This can prevent a display of an overlaid image having an uncertain positional relationship and also display a latest image of overlaid images subjected to the alignment. Since X-ray irradiation is stopped, an unnecessary subject's exposure can be avoided.

When the injection of the contrast medium is started, the intermediate image generation phase shifts to the blood vessel display phase. Whether the injection of the contrast medium has been started can be determined, for example, based on a signal (FIG. 1) indicating the injection of the contrast medium from an injector that injects the contrast medium. Alternatively, in the taken X-ray image, the injection of the contrast medium may be detected to determine whether the injection of the contrast medium has been started.

A shift from the intermediate image generation phase to the blood vessel display phase may be made on the conditions other than those for start of the injection of the contrast medium. For example, a phase shift may be made, for example, when the number of frames of X-ray images generated from the start of X-ray irradiation exceeds a predetermined number or when a predetermined period of time has elapsed from the start of X-ray irradiation. Such conditions being satisfied and the injection of the contrast medium being started correspond to "predetermined conditions" being satisfied in the present invention.

Figure 4:
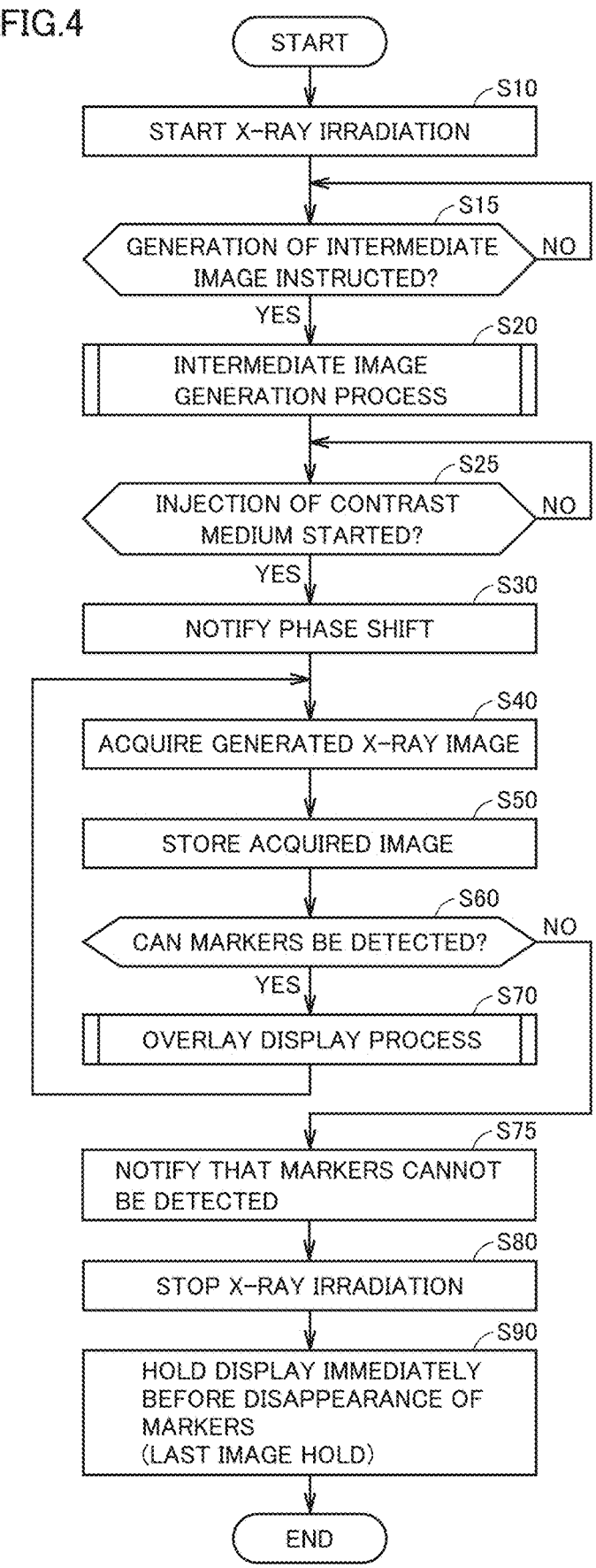
FIG. 4 is a flowchart showing an example procedure of processes performed by a control device shown in FIG. 1.

FIG. 4 is a flowchart showing an example procedure of processes performed by control device 32 shown in FIG. 1. A series of processes shown in this flowchart are started when the user inputs a start of the processes through operation device 50.

Referring to FIG. 4, control device 32 starts X-ray irradiation from X-ray irradiation device 14 to start X-ray imaging of subject 18 by imaging apparatus 10 (step S10). When X-ray irradiation has been started, control device 32 determines whether the generation of an intermediate image has been instructed (step S15). This instruction to generate an intermediate image can be input by the user through operation device 50 (FIG. 1). When the generation of an intermediate image has been instructed (YES at step S15), control device 32 performs an intermediate image generation process of generating an intermediate image (step S20).

Figure 5:
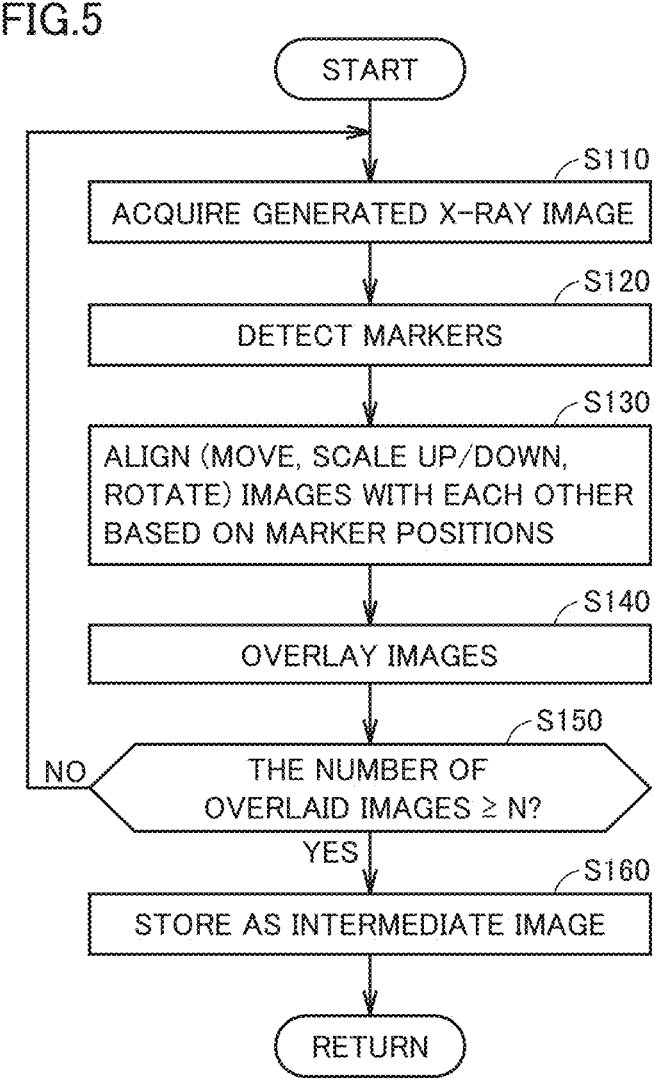
FIG. 5 is a flowchart showing an example procedure of an intermediate image generation process performed at step S20 of FIG. 4.

FIG. 5 is a flowchart showing an example procedure of the intermediate image generation process performed at step S20 of FIG. 4. Referring to FIG. 5, control device 32 acquires an X-ray image newly generated by X-ray image generation device 22 (step S110). X-ray image generation device 22 generates, for example, X-ray images of 15 frames per second.

When an X-ray image has been acquired from X-ray image generation device 22, control device 32 detects a pair of markers 63 (FIG. 2) from the acquired X-ray image (step S120). Various known image recognition techniques can be used as the technique of detecting markers 63. In the intermediate image generation phase, the visibility of markers 63 is high because the contrast medium has not been injected, and accordingly, markers 63 can be detected easily.

When markers 63 have been detected, control device 32 aligns the X-ray image acquired this time at step S110 and X-ray images acquired so far (if images have been overlaid on one another, an overlaid image obtained so far) with one another based on the positions of the detected markers 63 (step S130). Specifically, based on the positions of a pair of markers 63 detected at step S120 and the positions of pairs of markers 63 in the X-ray images acquired so far, the images are aligned with each other by matching the positions of the markers in both the images with each other.

When the X-ray image acquired at step S110 is a first image (first frame), the X-ray image can be overlaid on no image, and accordingly, the processes of step S130 and step S140, which will be described below, are omitted.

When images have been aligned with each other, control device 32 generates an overlaid image obtained by overlaying the X-ray images acquired so far (if images have been overlaid on one another, an overlaid image acquired so far) on the X-ray image acquired this time at step S110 (step S140).

Control device 32 then determines whether the number of images overlaid on the overlaid image generated at step S140 is N (e.g., eight to a dozen or so images) or more (step S150). If the number of images is less than N (NO at step S150), control device 32 returns the process to step S110 and waits for the acquisition of a next X-ray image from X-ray image generation device 22.

If determining that the number of images is N or more at step S150 (YES at step S150), control device 32 stores the generated overlaid image in storage 34 (FIG. 1) as an intermediate image (step S160).

Again referring to FIG. 4, when an intermediate image has been generated at step S20, control device 32 determines whether the injection of the contrast medium has been started (step S25). If determining that the injection of the contrast medium has been started (YES at step S25), control device 32 performs a process of notifying the user that the intermediate image generation phase will shift to the blood vessel display phase (step S30). For example, control device 32 controls display 40 to display that a phase shift is to be made. A phase shift may be notified, for example, by voice.

After the shift to the blood vessel display phase, control device 32 acquires an X-ray image newly generated by X-ray image generation device 22 (step S40). An X-ray image acquired after the shift to the blood vessel display phase is an image in which a blood vessel visualized by the injection of the contrast medium is displayed. Control device 32 then stores the acquired X-ray image in storage 34 (FIG. 1) (step S50).

Control device 32 then determines whether markers 63 can be detected in the X-ray image acquired at step S40 (step S60). When the contrast medium is injected into a blood vessel, the blood vessel is visualized, whereas the visibility of markers 63 decreases. As the injection of the contrast medium progresses, markers 63 can no longer be detected in the X-ray image.

If markers 63 can be detected in the acquired X-ray image (YES at step S60), control device 32 performs an overlay display process of displaying the intermediate image generated in the intermediate image generation process and a new X-ray image acquired at step S40 while overlaying the intermediate image on the X-ray image (step S70).

Figure 6:
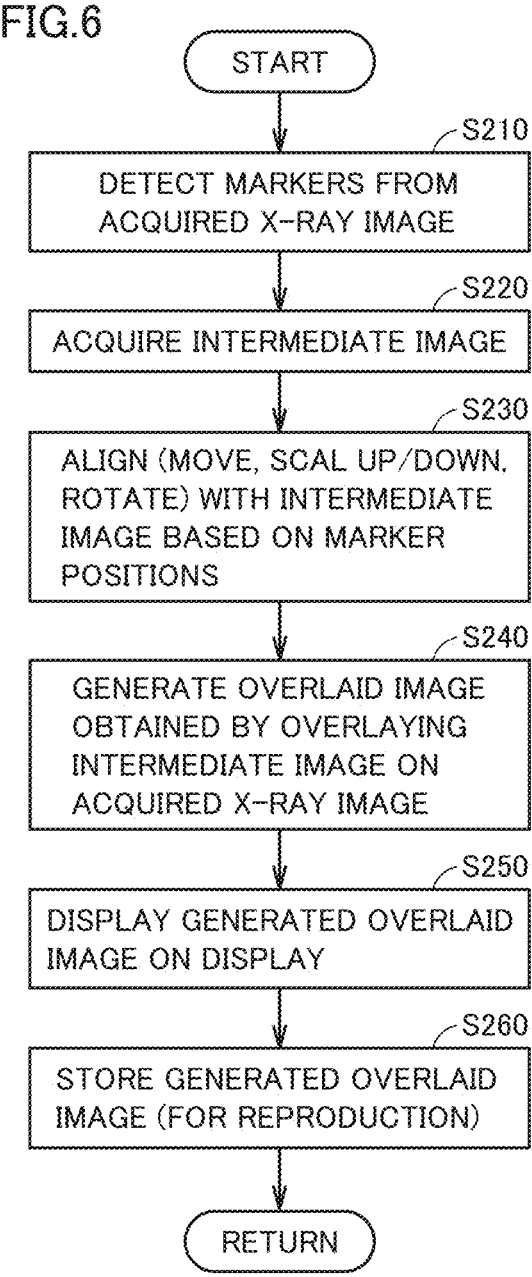
FIG. 6 is a flowchart showing an example procedure of an overlay display process performed at step S70 of FIG. 4.

FIG. 6 is a flowchart showing an example procedure of the overlay display process performed at step S70 of FIG. 4. Referring to FIG. 6, control device 32 detects a pair of markers 63 (FIG. 2) from the X-ray image acquired at step S40 of FIG. 4 (step S210). Control device 32 then acquires the intermediate image generated in the intermediate image generation process at step S20 of FIG. 4 from storage 34 (FIG. 1) (step S220).

Control device 32 then aligns a new X-ray image acquired this time at step S40 of FIG. 4 and the intermediate image with each other based on the positions of markers 63 detected at step S210 (step S230). Specifically, control device 32 also detects a pair of markers 63 from the intermediate image and match the positions of the markers in the intermediate image with the positions of markers 63 detected at step S210, thereby aligning a newly acquired X-ray image and the intermediate image with each other. More specifically, an image is moved, scaled up or down, or rotated so as to overlay markers 63 detected at step S210 and markers 63 of the intermediate image on each other, thereby aligning the images with each other.

When the images have been aligned with each other, control device 32 generates an overlaid image obtained by overlaying the intermediate image on a new X-ray image acquired at this time (step S240). Control device 32 then controls display 40 to display the generated overlaid image on display 40 (step S250). Control device 32 also stores the overlaid image generated at step S240 in storage 34 (FIG. 1) such that the generated overlaid image can be reproduced in display 40 after collection and display of a series of X-ray images (step S260).

Again referring to FIG. 4, when the overlay display process has been performed at step S70, control device 32 returns the process to step S40 and waits for the acquisition of a next X-ray image newly generated by X-ray image generation device 22.

If markers 63 cannot be detected in the acquired X-ray image at step S60 (NO at step S60), control device 32 performs a process for notifying the user that markers 63 cannot be detected in the acquired X-ray image (step S75). For example, control device 32 controls display 40 to display that markers 63 have not been detected. This notification may be made, for example, by voice.

Further, control device 32 outputs an instruction to operation device 50 to stop the X-ray irradiation from X-ray irradiation device 14 (step S80). Control device 32 then controls display 40 to hold display of display 40 immediately before markers 63 cannot be detected (step S90). In other words, an overlaid image (last image) of a latest X-ray image in which markers 63 have been detected and an intermediate image is held in display 40 (last image hold).

Figure 7:
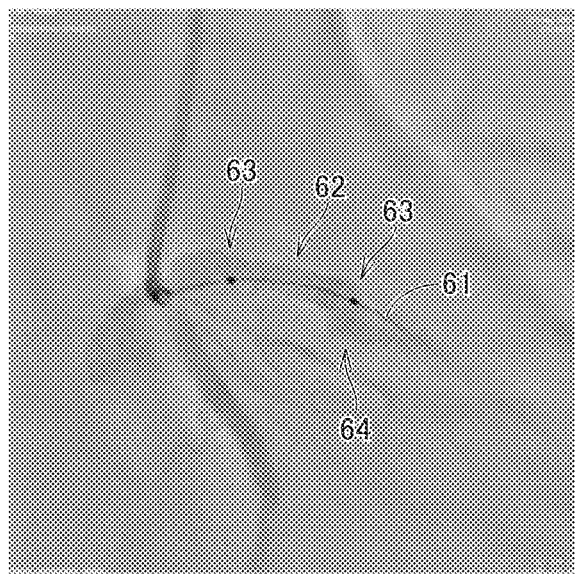
FIG. 7 shows an example display mode of an overlaid image displayed on a display in a blood vessel display phase.
Figure 8:
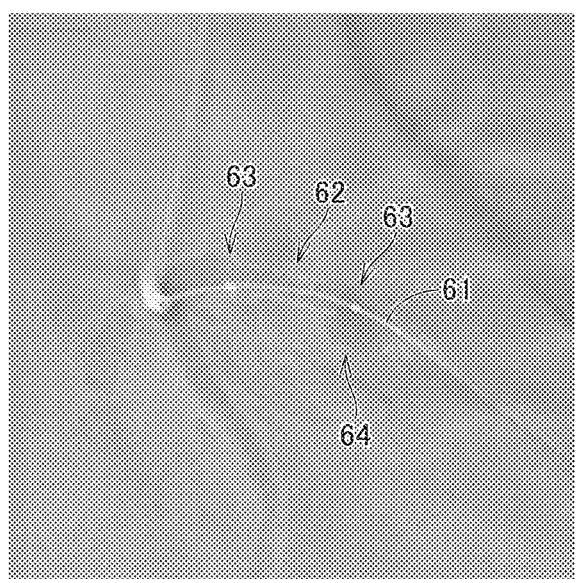
FIG. 8 shows another example display mode of an overlaid image displayed on the display in the blood vessel display phase.
Figure 9:
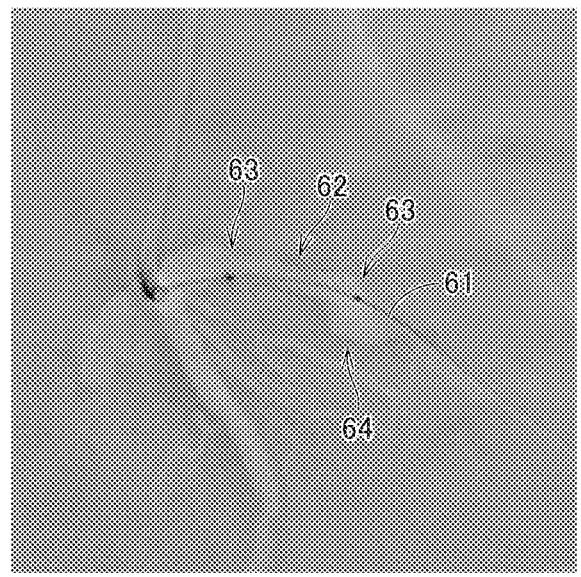
FIG. 9 shows still another example display mode of an overlaid image displayed on the display in the blood vessel display phase.

FIGS. 7 to 9 show an example display mode of an overlaid image displayed on display 40 at step S250 of FIG. 6.

Referring to FIG. 7, in this example, control device 32 generates an overlaid image by causing the transmittance of an X-ray image newly generated after the injection of the contrast medium and the transmittance of the intermediate image to vary from each other and overlaying these images on each other, and then causes display 40 to display the overlaid image. A lower transmittance results in a darker (less transmissive) image, and a higher transmittance results in a brighter (more transmissive) image. As shown in FIG. 7, displaying both images while appropriately varying their transmittances from each other allows both of a blood vessel 64 displayed in the acquired X-ray image and device 62 displayed in the intermediate image to be visually recognized clearly on the overlaid image. The transmittance of the X-ray image acquired and the transmittance of the intermediate image may be changed by the user through operation device 50.

Referring to FIG. 8, in this example, control device 32 generates an overlaid image by reversing black and white of an intermediate image and overlays the intermediate image on the acquired X-ray image, and causes display 40 to display the overlaid image. Referring to FIG. 9, in this example, control device 32 overlays the intermediate image on the image obtained by reversing black and white of the acquired X-ray image to generate an overlaid image, and causes display 40 to display the overlaid image. In this manner, an overlaid image is displayed by reversing black and white of any one of the acquired X-ray image and the intermediate image and overlaying these images on each other, so that both of blood vessel 64 displayed on the acquired X-ray image and device 62 displayed on the intermediate image can be visually recognized clearly on the overlaid image.

In another example, control device 32 may generate an overlaid image by causing a display color of an X-ray image newly generated after the injection of the contrast medium and a display color of the intermediate image to vary from each other and overlaying these images and cause display 40 to display the overlaid image. The overlaid image generated in this manner also allows blood vessel 64 displayed in the acquired X-ray image and device 62 displayed in the intermediate image to be virtually recognized while these images are clearly distinguished from each other.

In the present embodiment, after imaging of a series of X-ray images is complete, an overlaid image generated in the blood vessel display phase can be acquired from storage 34 in response to a reproduction request and continuously reproduced in display 40. The reproduction request may be, for example, a request from a user through operation device 50 (FIG. 1) or a request automatically issued at a predetermined timing after imaging of a series of X-ray images is complete.

Figure 10:
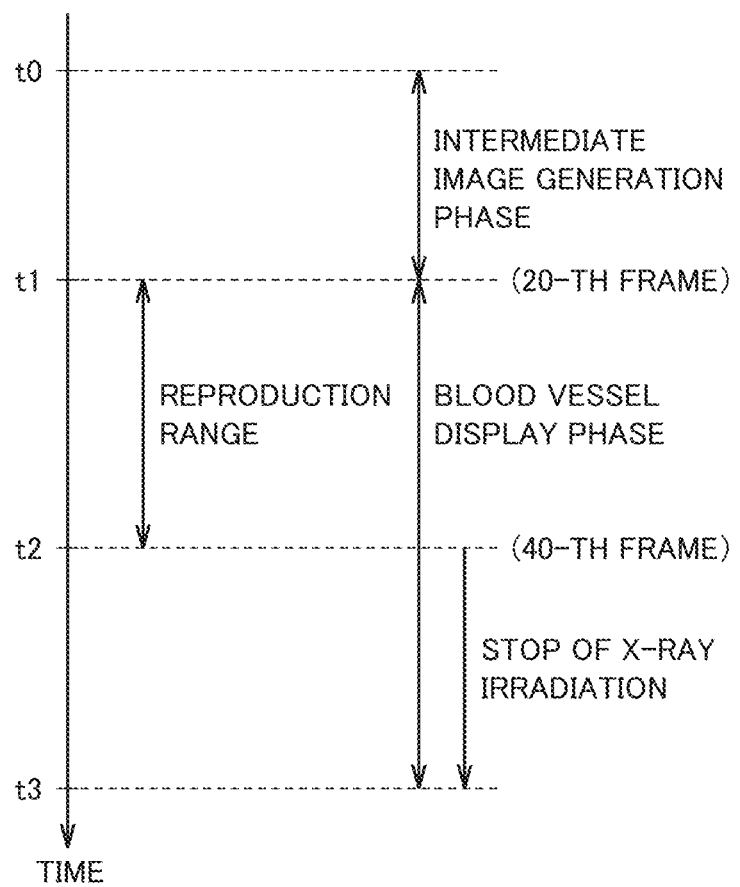
FIG. 10 shows a reproduction range of an overlaid image continuously reproduced in the display after the completion of imaging of a series of X-ray images.

FIG. 10 shows a reproduction range of an overlaid image continuously reproduced in display 40 after imaging of a series of X-ray images is complete. Referring to FIG. 10, for example, a phase from start of imaging by imaging apparatus 10 at time t0 to a 20-th frame is the intermediate image generation phase, and when injection of the contrast medium is started at time t1, the intermediate image generation phase shifts to the blood vessel display phase from 21-th frame. When markers 63 can no longer be detected in an acquired image of a 41st frame in the blood vessel display phase (time t2), the images from 21st frame to 40-th frame are selected as the reproduction range.

FIG. 11 is a flowchart showing an example procedure of the image reproduction process performed by control device 32. The process shown in this flowchart is started in response to a reproduction request after imaging of a series of X-ray images is complete.

With reference to FIG. 11, control device 32 acquires a series of overlaid images generated in the overlay display process of FIG. 6 and stored in storage 34 from storage 34 in response to a reproduction request (step S310). Control device 32 then controls display 40 to continuously reproduce the series of overlaid images acquired from storage 34 in display 40 (step S320).

As described above, the present embodiment allows, after the generation of an intermediate in which displaying device 62 is displayed, a new X-ray image and the intermediate image to be aligned with each other based on the positions of markers 63 every time an X-ray image is newly generated, and then, allows display of an overlaid image on display 40 in real time. Consequently, an intervention treatment can be performed while checking the state of subject 18 on display 40 in real time.

The present embodiment displays an overlaid image of a latest X-ray image in which markers 63 are detected and the intermediate image when markers 63 can no longer be detected in a newly generated X-ray image due to the progress of the injection of the contrast medium in the blood vessel display phase (last image hold). The present embodiment can thus prevent display of an overlaid image having an uncertain positional relationship and display, on display 40, a latest image of the overlaid images subjected to the alignment. Further, the present embodiment stops X-ray irradiation when markers 63 can no longer be detected, avoiding unnecessary exposure of subject 18.

In the present embodiment, an intermediate image is generated by overlaying a plurality of X-ray images in which device 62 is displayed on one another in the intermediate image generation phase, so that device 62 is displayed while being highlighted in the intermediate image. This allows device 62 to be visually recognized clearly in the overlaid image.

[Variation 1]

In the embodiment above, when markers 63 can no longer be detected in a newly generated X-ray image in the blood vessel display phase, an overlaid image of a latest X-ray image in which markers 63 are detected and an intermediate image is displayed (last image hold). Alternatively, an image having the highest contrast among the X-ray images in which markers 63 are detected may be selected and overlaid on an intermediate image to be displayed on display 40.

FIG. 12 is a flowchart showing an example procedure of processes performed by control device 32 in Variation 1. This flowchart corresponds to the flowchart of FIG. 4 in the above embodiment. A series of processes shown in this flowchart are also started when, for example, the user inputs start of the processes through operation device 50.

Referring to FIG. 12, the processes of steps S410 to S480 are identical to the processes of steps S10 to S80 shown in FIG. 4, respectively. In Variation 1, when X-ray irradiation is stopped at step S480, control device 32 acquires an image having the highest contrast from storage 34 from among the overlaid images generated so far in the blood vessel display phase (step S485). Control device 32 then controls display 40 to display the acquired overlaid image having the highest contrast (step S490).

Variation 1 can also prevent display of an overlaid image having an uncertain positional relationship when marker 63 cannot be detected due to the injection of the contrast medium. Variation 1 can display, on display 40, an image having the highest contrast among the overlaid images subjected to the alignment.

[Variation 2]

Although X-ray irradiation is stopped when markers 63 can no longer be detected in an X-ray image newly generated in the blood vessel display phase in the above embodiment and Variation 1, X-ray images newly generated may be sequentially displayed on display 40 and stored in storage 34 without stopping the X-ray irradiation until stop of X-ray imaging is instructed. An X-ray image newly generated and the intermediate image cannot be aligned with each other because markers 63 cannot be detected; however, generated X-ray images are displayed and stored until the completion of X-ray imaging is instructed.

FIG. 13 is a flowchart showing an example procedure of processes performed by control device 32 in Variation 2. This flowchart also corresponds to the flowchart of FIG. 4 in the above embodiment. A series of processes shown in this flowchart are started when, for example, the user inputs a start of the processes through operation device 50.

With reference to FIG. 13, the processes of steps S510 to S575 are identical to the processes of steps S10 to S75 shown in FIG. 4, respectively. In Variation 2, when detection of no markers 63 is notified at step S575, control device 32 continuously acquires an X-ray image newly generated by X-ray image generation device 22 (step S580).

Control device 32 then causes display 40 to display the acquired X-ray image on and stores them in storage 34 (FIG. 1) (step S585). Control device 32 then determines whether X-ray imaging is complete (step S590). The completion of X-ray imaging can be instructed, for example, by the user through operation device 50.

If X-ray imaging is not complete (NO at step S590), control device 32 returns the process to step S580 and waits for the acquisition of a next X-ray image generated by X-ray image generation device 22. If determining that X-ray imaging is complete at step S590 (YES at step S590), control device 32 moves the process to END to end the series of processes.

Even when markers 63 can no longer be detected due to the injection of the contrast medium and an acquired X-ray image and the intermediate image cannot be aligned with each other in the blood vessel display phase, Variation 2 can display newly generated X-ray images on display 40 and store them in storage 34 without stopping X-ray irradiation until an end of X-ray imaging is instructed.

Although an image subjected to last image hold when markers 63 can no longer be detected in an X-ray image due to the injection of the contrast medium is an image obtained by overlaying a latest X-ray image in which markers 63 are detected and the intermediate image on each other (embodiment) or an image obtained by overlaying an image having the highest contrast among the X-ray images in which markers 63 are detected and the intermediate image on each other (Variation 1) in the above description, embodiments of the present invention are not limited thereto. It suffices that a last-image-hold image in the embodiments of the present invention is an image in which the relative positions of device 62 and blood vessel 64 can be recognized.

Lastly, the radiographic system disclosed in the present embodiment will be summarized.

A radiographic system (100) according to embodiments of the present invention includes an imaging apparatus (10) configured to irradiate a subject (18) with X-rays and sequentially generate an X-ray image of the subject, a display (40) configured to display the X-ray image generated by the imaging apparatus, and a controller (30) configured to control the display. The controller generates, based on a position of a marker (63) in the X-ray image, an intermediate image in which a device (62) is displayed from the X-ray image, where the device (62) is inserted into a body of the subject. After the generation of the intermediate image, the controller matches the marker in the X-ray image with a marker in the intermediate image based on the position of the marker in the X-ray image and a position of the marker in the intermediate image to align the X-ray image and the intermediate image with each other every time the X-ray image is newly generated. The controller then controls the display to display an overlaid image generated by overlaying the X-ray image and the intermediate image aligned with each other.

This radiographic system can align, after the generation of the intermediate image in which the device is displayed, the X-ray image and the intermediate image with each other and then display the overlaid image on the display in real time every time the X-ray image is newly generated. Consequently, an intervention treatment can be performed while checking the subject's state in real time.

When the marker is not detected in the X-ray image, the controller may control the display to display the overlaid image generated using a latest X-ray image in which the marker is detected.

This radiographic system cannot align an X-ray image in which the marker cannot be detected and the intermediate image with each other, and accordingly, displays an overlaid image of the intermediate image and a latest X-ray image in which the marker is detected, in place of a newly generated X-ray image. This radiographic system can thus prevent display of an overlaid image having an uncertain positional relationship and display a latest image among the overlaid images aligned with each other.

When the marker is not detected in the X-ray image, the controller may control the display to display the overlaid image generated using an X-ray image having the highest contrast among X-ray images in which the marker is detected.

This radiographic system cannot align an X-ray image, in which a marker cannot be detected, and the intermediate image with each other, and accordingly, displays an overlaid image of the intermediate image and an image having the highest contrast among the X-ray images in which the marker has bee detected, in place of a newly generated X-ray image. This radiographic system can thus prevent display of an overlaid image having an uncertain positional relationship and display an image having the highest contrast among the overlaid images subjected to the alignment.

When the marker is not detected in the X-ray image, the controller may control the imaging apparatus to stop X-ray irradiation.

Thus, unnecessary exposure of a subject can be avoided. Since no overlaid image is generated from an X-ray image in which the marker is not detected, display on the display is not affected even when X-ray irradiation is stopped.

When the marker is not detected in the X-ray image, the controller may control the display to display that the marker is not detected.

Thus, the user of the radiographic system can recognize that display contents are to be changed (real-time display, performed every time an X-ray image is newly generated, is no longer provided) because the marker cannot be detected in an X-ray image.

The controller may align, based on the position the marker in each of a plurality of the X-ray images in which the device is displayed, the plurality of X-ray images with each other, and generate the intermediate image by overlaying the plurality of X-ray images aligned with each other.

Since the device is accordingly displayed while being highlighted in the intermediate image, the device can be visually checked clearly in the overlaid image.

The controller may generate the intermediate image based on an X-ray image generated before a predetermined condition is satisfied.

This allows automatic generation of the intermediate image based on the X-ray image generated before the condition is satisfied, which is triggered by satisfaction of the predetermined condition.

The predetermined condition may be satisfied when injection of a contrast medium into the subject is started from an apparatus for injecting the contrast medium into the subject.

The predetermined condition may be satisfied when injection of a contrast medium into the subject is detected in the X-ray image generated by the imaging apparatus.

This allows automatic generation of an intermediate image based on the X-ray image taken before the injection of the contrast medium, which is triggered by injection of the contrast medium.

The controller may generate the overlaid image by causing transmittances of the X-ray image and the intermediate image aligned with each other to vary from each other and overlaying the X-ray image and the intermediate image.

The controller may generate the overlaid image by reversing black and white of any one of the X-ray image and the intermediate image aligned with each other and overlaying the X-ray image and the intermediate image.

The controller may generate the overlaid image by causing display colors of the X-ray image and the intermediate image aligned with each other to vary from each other and overlaying the X-ray image and the intermediate image.

According to the above, the display target displayed in the X-ray image and the device displayed in the intermediate image can be visually checked while these images are clearly differentiated from each other.

The controller may control, upon generation of the intermediate image, the display to display that the overlaid image is started to be displayed.

This allows the user of the radiographic system to recognize a shift from a phase (intermediate image generation phase) in which an intermediate image is generated to another phase (blood vessel display phase) in which an overlaid image is displayed.

The controller may control the display to continuously reproduce the overlaid image in response to a reproduction request after the generation of the X-ray image by the imaging apparatus is complete.

This allows only the X-ray image aligned with the intermediate image to be reproduced and displayed in the display in response to a reproduction request from the user or the like.

The device may be a stent inserted into a blood vessel (64) of the subject. The controller may generate the intermediate image before a contrast medium is injected into the blood vessel of the subject and, after the generation of the intermediate image, align the X-ray image and the intermediate image with each other every time the X-ray image taken with the contrast medium injected into the blood vessel of the subject is newly generated, and control the display to display the overlaid image.

This radiographic system enables an intervention treatment while checking the positional relationship between a stent inserted into a blood vessel of a subject and a blood vessel in real time.

The embodiments disclosed herein are illustrative and non-restrictive in any respect. The scope of the present invention is defined by the terms of the claims, rather than the embodiments described above, and is intended to include any modifications within the scope and meaning equivalent to the terms of the claims.

What is claimed is:

1. A radiographic system comprising:
    an imaging apparatus configured to irradiate a subject with X-rays and sequentially generate X-ray images of the subject;
    a display configured to display the X-ray images generated by the imaging apparatus; and
    a controller configured to the display,
    wherein the controller is configured to
        generate, from the X-ray images before injection of a contrast medium, an intermediate image in which a device is displayed while being highlighted in the intermediate image, the device being inserted into a body of the subject
        store the generated intermediate image in a storage,
    sequentially generate a series of overlaid images by overlaying the X-ray images after injection of the contrast medium on the intermediate image stored in the storage, and
    control the display to sequentially display the generated series of overlaid images,
    wherein a shift from a process in which the intermediate image is generated to a process in which the overlaid images are sequentially generated is made when a predetermined condition is satisfied.

2. The radiographic system according to claim 1, wherein the controller is configured to, when the marker is not detected in the X-ray image, control the display to display the overlaid image generated using a latest X-ray image in which the marker is detected.

3. The radiographic system according to claim 2, wherein the controller is configured to, when the marker is not detected in the X-ray image, control the imaging apparatus to stop X-ray irradiation.

4. The radiographic system according to claim 2, wherein the controller is configured to, when the marker is not detected in the X-ray image, control the display to display that the marker is not detected.

5. The radiographic system according to claim 1, wherein the controller is configured to, when the marker is not detected in the X-ray image, control the display to display the overlaid image generated using an X-ray image with a highest contrast among X-ray images in which the marker is detected.

6. The radiographic system according to claim 1, wherein the controller is configured to
    based on the position of the marker in each of a plurality of the X-ray images in which the device is displayed, align the plurality of X-ray images with each other, and generate the intermediate image by overlaying the plurality of X-ray images aligned with each other.

7. The radiographic system according to claim 1, wherein the predetermined condition is satisfied when injection of a contrast medium into the subject is started from an apparatus for injecting the contrast medium into the subject.

8. The radiographic system according to claim 1, wherein the predetermined condition is satisfied when injection of a contrast medium into the subject is detected in the X-ray image generated by the imaging apparatus.

9. The radiographic system according to claim 1, wherein the controller is configured to generate the overlaid image by causing transmittances of the X-ray image and the intermediate image aligned with each other to vary from each other and overlaying the X-ray image and the intermediate image.

10. The radiographic system according to claim 1, wherein the controller is configured to generate the overlaid image by reversing black and white of any one of the X-ray image and the intermediate image aligned with each other and overlaying the X-ray image and the intermediate image.

11. The radiographic system according to claim 1, wherein the controller is configured to generate the overlaid image by causing display colors of the X-ray image and the intermediate image aligned with each other to vary from each other and overlaying the X-ray image and the intermediate image.

12. The radiographic system according to claim 1, wherein the controller is configured to control, upon generation of the intermediate image, the display to display that the overlaid images are started to be displayed.

13. The radiographic system according to claim 1, wherein the controller is configured to control the display to continuously reproduce the overlaid image in response to a reproduction request after the generation of an X-ray image by the imaging apparatus is complete.

14. The radiographic system according to claim 1, wherein the device is a stent inserted into a blood vessel of the subject, and the controller is configured to
    generate the intermediate image before a contrast medium is injected into the blood vessel of the subject,
    after the generation of the intermediate image, align the X-ray image and the intermediate image with each other every time the X-ray image taken with the contrast medium injected into the blood vessel of the subject is generated, and control the display to display the overlaid image.

15. A radiographic system comprising:
    an imaging apparatus configured to irradiate a subject with X-rays and sequentially generate X-ray images of the subject;
    a display configured to display the X-ray images generated by the imaging apparatus; and
    a controller configured to control the display, wherein the controller is configured to generate an intermediate image in which a device is displayed from an intermediate X-ray image, the device having a marker and being inserted into a body of the subject, after the generation of the intermediate image, generating with the imaging apparatus new X-ray images of the device having the marker in the subject, wherein from each new X-ray image, the marker in each new X-ray image is matched with the marker in the intermediate image based on a position of the marker in the new X-ray image and a position of the marker in the intermediate image to align the new X-ray image and the intermediate image with each other every time a new X-ray image is newly generated, and control the display to display a series of overlaid images generated by overlaying each new X-ray image and the intermediate image aligned with each other, wherein the display displays a new overlaid image as each new X-ray image is generated by the imaging apparatus;

and wherein the intermediate image is formed from a plurality of intermediate X-ray images generated prior to a contrast medium being injected into a blood vessel of the subject, and wherein the intermediate X-ray images are aligned and overlaid with each other as they are generated by the imaging apparatus.

16. The radiographic system according to claim 15, wherein each new overlaid image is generated and displayed in real time every time a new X-ray image is generated by the imaging apparatus.

17. The radiographic system according to claim 15, wherein every time a new X-ray image is newly generated, if the marker appear in the new X-ray image, a new overlaid image generated by overlaying the new X-ray image and the intermediate image is displayed on the display.

18. The radiographic system according to claim 15, wherein a number of the plurality of intermediate X-ray images generated prior to injection of a contrast medium into the blood vessel of the subject is a predetermined number, and wherein a number of new X-ray images generated after a start of injection of a contrast medium into the blood vessel of the subject is dependent upon a detectability of the marker.

* * * * *